United States Patent
Timmermann et al.

(10) Patent No.: US 11,426,491 B2
(45) Date of Patent: Aug. 30, 2022

(54) LAYER HAVING VARIABLE STRENGTH

(71) Applicant: Universitaet Heidelberg, Heidelberg (DE)

(72) Inventors: Michael Timmermann, Kiel (DE); Soeren Gutekunst, Kiel (DE); Christine Selhuber-Unkel, Kiel (DE); Eckhard Quandt, Heikendorf (DE)

(73) Assignee: Universitaet Heidelberg, Heidelberg (DE)

( * ) Notice: Subject to any disclaimer, the term of this patent is extended or adjusted under 35 U.S.C. 154(b) by 307 days.

(21) Appl. No.: 16/094,553

(22) PCT Filed: Mar. 23, 2017

(86) PCT No.: PCT/DE2017/100238
§ 371 (c)(1),
(2) Date: Oct. 18, 2018

(87) PCT Pub. No.: WO2017/182024
PCT Pub. Date: Oct. 26, 2017

(65) Prior Publication Data
US 2019/0117845 A1 Apr. 25, 2019

(30) Foreign Application Priority Data
Apr. 22, 2016 (DE) .................... 10 2016 107 480.2

(51) Int. Cl.
*A61L 27/50* (2006.01)
*A61L 27/54* (2006.01)

(52) U.S. Cl.
CPC ............ *A61L 27/507* (2013.01); *A61L 27/50* (2013.01); *A61L 27/54* (2013.01); *A61F 2250/0018* (2013.01); *A61F 2250/0051* (2013.01); *A61L 2400/18* (2013.01)

(58) Field of Classification Search
CPC ......... A61F 2250/0018; A61L 2400/18; A61L 27/50; A61L 27/507; A61L 27/54
See application file for complete search history.

(56) References Cited

U.S. PATENT DOCUMENTS

| | | | |
|---|---|---|---|
| 8,072,437 B2 | 12/2011 | Miller et al. | |
| 8,454,566 B2 * | 6/2013 | Van Antwerp | A61L 29/085 604/265 |
| 2003/0055496 A1 * | 3/2003 | Cai | A61F 2/2412 623/2.19 |
| 2004/0063200 A1 * | 4/2004 | Chaikof | C08F 220/28 435/317.1 |
| 2005/0037189 A1 | 2/2005 | Palmer et al. | |
| 2010/0205722 A1 * | 8/2010 | Kim | B32B 9/025 2/455 |

FOREIGN PATENT DOCUMENTS

DE 60222805 T2 7/2008

OTHER PUBLICATIONS

Selhuber et al. (Nano Letters, 2006 vol. 6, No. 2 267-270). (Year: 2006).*
International Search Report dated Jul. 26, 2017, in International Application No. PCT/DE2017/100238.

* cited by examiner

*Primary Examiner* — Anna R Falkowitz
(74) *Attorney, Agent, or Firm* — Patent Central LLC; Stephan A. Pendorf

(57) ABSTRACT

A layer having individual elements made of an elastic material, with the length thereof exceeding the diameter thereof, which are secured on a carrier at a distance to one another, wherein the elements can be moved towards and away from one another, the elements can contact when moving towards one another, the outer surfaces of the elements provided with a surface modification, and the surface modification containing substances that can form reversible, non-covalent bonds. Also, a method for producing the layer, and the use of the layer.

5 Claims, 2 Drawing Sheets

LAYER HAVING VARIABLE STRENGTH

Figure 1:
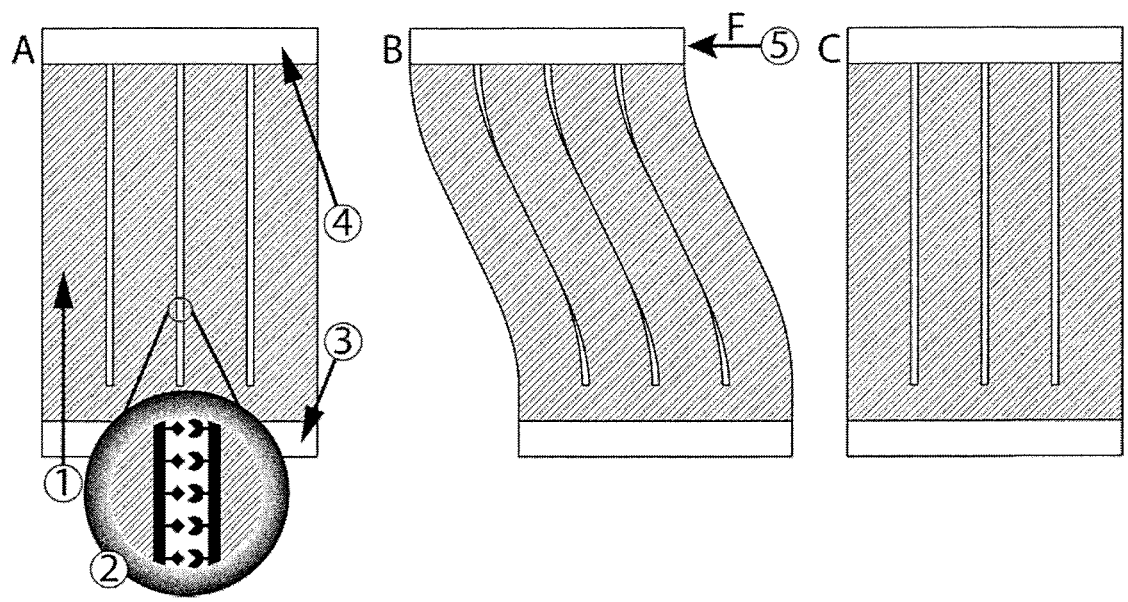

The invention relates to a layer which is able, upon the application of an external force, to increase its stiffness abruptly once the external force has reached a certain value, and to return to the original state upon release of this external force. The invention relates to a method for producing this layer and to the use of the layer as a shock-absorbing agent, for the production of vascular prostheses with nonlinear elastic behavior and for flexible display devices.

The behavior of increasing stiffness under the application of an external force is known as "strain stiffening". Some body tissues, such as the aorta, exhibit "strain-stiffening" behavior. Corresponding materials can offer better substitution than materials with linear elasticity behavior (or even "strain softening"). [Qi Wen, Paul A. Janmey, Effects of non-linearity on cell ECM interactions, Experimental Cell Research, Volume 319, Issue 16, 1 Oct. 2013, pp. 2481-2489, ISSN 0014-4827, http://dx.doi.org/10.1016/j.yexcr.2013.05.017].

The content of the pamphlets "Self-Healing Polymers: From Principles to Applications, First Edition. Edited by Wolfgang H. Binder © 2013 Wiley-VCH Verlag GmbH & Co. KGaA. Published 2013 by Wiley-VCH Verlag GmbH & Co. and Kim et al. Biomicrofluidics 7, 041501 (2013) doi: 10.1063/1.4816934 and pence et al Biomater Sci 2014, 2, 1296-1304 (DOI: 10.1039/c4bm00193a) is explicitly incorporated by reference.

US 2003/0055496 A1 proposes a vascular prosthesis with nonlinear elastic behavior, in which the nonlinear elastic behavior is caused by textile entanglements of the outer layer. From the medical point of view very desirable nonlinear elastic behavior, but limits are set in the system by the geometry and size of the textile entanglements.

US 2010/0205722 describes a shock-absorbing layer in which several isolated, regularly arranged, flexible elements come into contact with a less flexible grid, there is a distribution of the impact force over a larger area and thus to an impact and shock absorbing effect. The disadvantage of these systems is the low flexibility of the systems.

DE 60222805 T2 therefore proposes the use of dilatant fluids in the context of an energy-absorbing composite. The system is limited by the use of the fluid and not suitable for very thin layers.

Flexible multitouch displays are known from U.S. Pat. No. 8,072,437 B2, in which it would be great advantage to have a layer to protect the sensors, which, upon application of an external force above a certain value, solidifies, and when the external force ceases, the original flexibility immediately returns. In these n systems, it is crucial to be able to keep the dimensions small, preferably in a range of less than 100 μm.

It is therefore an object of the invention to provide a layer which is capable, upon application of an external force, to increase its stiffness abruptly, once the external force has reached a certain value, and to return to its original state upon release of this external force.

Furthermore, it is an object of the invention to provide a layer which is able to increase its stiffness under the influence of an external force, as soon as the external force has reached a certain value, and to return to its original state upon release of this external force, and which can have dimensions of less than 100 μm.

A further object of the invention is to provide a method for producing a layer capable of, upon application of an external force, increasing its stiffness abruptly once the external force has reached a certain value, and on release of this external force returning back to the original state.

A further object of the invention is to provide a method for producing a layer capable of, upon application of an external force, increasing its stiffness abruptly once the external force has reached a certain value, and on release of this external force returning back to the original state (relaxing), which provides an adaptability of the stiffness to the acting forces, which allows the necessary stiffening and relaxation behavior.

The object of the invention is achieved on the one hand by a layer having individual columnar elements made of an elastic material, with the length thereof exceeding the diameter thereof, which are secured on a carrier with a center-to-center distance from one another, characterized in that the elements can be moved towards and away from one another, the elements can contact when moving towards one another, the outer surfaces of the elements are provided with a surface modification, and the surface modification contains substances that can form reversible, non-covalent bonds.

The material has elements with their length surpassing their diameter (columns) made of an elastomer. They are designed so that an external force on the elements ensures that individual parts of the elements touch each other.

The outer surfaces of the elements have a surface modification which ensures that at the points where the contact takes place, a reversible connection of the parts results. The strength of the connection is chosen so that it releases as soon as the force previously applied to the material is removed and the material can return to the initial state (reversibility). The surface modification is not changed thereby.

The choice of the carrier material determines the initial mechanical properties of the material. The shape of the support material and the type of surface treatment determines the mechanical properties of the material in the case of deformation.

In one embodiment, it is preferable to use only biocompatible materials and thus to obtain a biocompatible product.

The principle of the layer according to the invention is shown schematically in FIG. 1. In FIG. 1A, the columnar elements (1), with a surface modification (2) fixed on the substrate (3), can be seen without influence of external force. The structure is covered by a cover plate (4). By external force (5), the elements are sheared, the elements touch each other (FIG. 1B). Due to the surface modification (2), reversible non-covalent bonds are formed, resulting in crosslinking and stiffening of the material. On release or elimination of external force (5), the system returns to its original state due to the restoring force due to the elastic properties of the elements (FIG. 1C).

Surface modification may be biofunctionalization, chemical functionalization, changes of surface topography, which ensure a mechanical cross-linking.

The surface modification (2) contains substances which are capable of forming reversible, non-covalent bonds. Such substances are generally known to those of ordinary skill in the art, for example from "Self-Healing Polymers: From Principles to Applications, First Edition. Edited by Wolfgang H. Binder © 2013 Wiley-VCH Verlag GmbH & Co. KGaA. Published 2013 by Wiley-VCH Verlag GmbH & Co. KG. Co. KGaA.

In one particular embodiment, the substances which are capable of forming reversible, non-covalent bonds may have a linkage between protein A and antibodies, Concanavalin A and α-D-glucose or streptavidin and biotin. Such systems are known to those of ordinary skill in the art from, for example, Kim et al. Biomicrofluidics 7, 041501 (2013) doi: 10.1063/1.4816934 and Pence et al. Biomater. Sci., 2014, 2, 1296-1304 (DOI: 10.1039/c4bm00193a).

Furthermore, chemical bonding concepts such as supramolecular structures with hydrogen bonds, π-π stacks, metal-ligand systems, or ionomers can be considered.

The elements are made of elastic materials. The property elasticity can be specified with the modulus of elasticity. For example, one of ordinary skill in the art will find elastic moduli of materials in the Materials Data Book 2003 Edition by Cambridge University Engineering Department.

The subsequent application of the layer according to the invention gives the required parameters, with the aid of the method according to the invention it becomes possible to select the materials, shapes and dimensions of the elements, as well as the surface modification.

For the production of the layer according to the invention, a method is used which first determines the parameters necessary for the subsequent material production, comprising the following steps:
i) determining the length of the elements (L) on the basis of the later application given overall dimensions and the achievable film thickness;
ii) the later application prescribes the basic rigidity of the layer, and based on this information, determining the material (via the modulus of elasticity), the shape and the diameter of the elements (via the plane inertia module I);
(iii) defining the desired deflection (A) until stiffening occurs on the basis of the necessary percentage stiffening of the layer;
(iv) determining of surface modification in terms of substances and concentration of substances under the proviso to ensure an adhesive force, which is below the return force $R_A$ given by the steps i to iii;
v) material preparation of the layer.

For the material production of the layer essentially two methods can be used.

Either the column spacings are set directly so that the final column spacing can be achieved with one casting, or another column spacing is chosen so that the final column spacing is achieved by nesting two samples.

Method. A - Finished Layer with One Casting:

This method is suitable for surface modifications where substances should be used which are compatible with themselves (e.g., cadherin-cadherin). It must be ensured that when combining the materials, the active ends of the substances used for surface modification are blocked so that the molecules bind to the surface and do not only react with themselves. The distances of the columnar elements are always the same after the application of method A and it eliminates the step of placing two sublayers into one another.

Step v Method A: Material Preparation of the Layer Comprising the Following Steps
  producing the mold taking into account the parameters determined in steps i to iii for the length, the arrangement, the shape and the diameter of the elements according to methods known to those of ordinary skill in the art
  applying a non-stick coating on the mold
  casting the mold with the material and modulus defined in step ii
  applying the surface modification in which according to step iv substances should be used, which bond with themselves (e.g., cadherin-cadherin).

It is important to ensure that when combining the materials, the active ends of the substances used for surface modification are blocked.

applying an adhesive
  adhering the cover plate (4)
  curing of the adhesive

Method B—Putting Two Partial Layers into Each Other:

In this method, surface modifications can be selected, in which two different substances, which together form a reversible, non-covalent bond (e.g., biotin-streptavidin) are used. In each case a partial layer is functionalized with one of the two substances. Afterwards both partial layers are put into each other.

Step v Method B: Material Preparation of the Layer Comprising the Following Steps
  production of one to two molds, taking into account the parameters determined in step i to iii for the length, arrangement, shape and diameter of the elements according to methods generally known to the person of ordinary skill in the art
  applying a non-stick coating on the molds
  casting into a mold a material and modulus defined in step ii
  casting another mold with the material and modulus defined in step ii
  applying for the surface modification two different substances determined according to step iv which form with each other a mutually reversible, non-covalent bond
  applying the adhesive
  interfacing the two sub-layers
  curing of the adhesive The production of the mold is carried out by methods well known to those of ordinary skill in the art. In addition to the method of reactive ion etching, lithography, in particular photolithography, may be used.

Non-stick coatings are well known to those of ordinary skill in the art, preferably a silane is used.

The casting of the mold is carried out according to well-known methods. Preferably, monomers or prepolymers are introduced into the mold together with a suitable "crosslinker" and thus cured by chemical means via polymerization reactions. When using this method, the amount of "crosslinker" can be used to set the modulus of elasticity of the material to the value previously determined. Curing can also take place in other ways that are generally known to the person of ordinary skill in the art, for example via a light-induced polymerization.

When adhering the cover plate (4), it has proved to be particularly advantageous to use as a "glue" uncrosslinked material of the same type as for casting of the mold. The procedure is as follows:
  immersing the pillar tips in non-crosslinked monomer or prepolymer—optionally with the addition of the crosslinker as an "adhesive", here care should be taken that only the tips can dip into the glue. This can be, for example, in that the monomer or prepolymer is made so thin by spin-coating on a glass plate so that only a part of the columns can dip (layer thickness can be up to 1 µm or thicker);
  affixing a cover layer, for example, of monomer or prepolymer, or glass.

Curing of the adhesive may take place at room temperature or—if the chosen surface modification allows it to be done—accelerated by heating or irradiation with a suitable light source.

In the following, the inventive method will be explained in more detail, and some examples are shown. A graphic representation of the relationships can be found in FIG. 2.

The return or restoring force RA of the columns is calculated from $R_A = EI\Delta/L^3$ with
E: modulus of elasticity of the plastic
I: 2nd-degree inertia modulus
$\Delta$: displacement of the columns
L: length of the columns Variations in the shape of the base area of the pillars lie in the area inertia module I:

$$e.g.: I_{round} = \pi d^4/64; I_{square} = h^4/12; I_{rectangle} = b \cdot h^3/12$$
(whith $h$:shorter side)

The restoring force $R_A$ counteracts the adhesive force of the bindings.

The adhesion force is calculated by determining the contact area of the columnar elements with each other. Since the columnar elements have a defined distance from each other both on top and below, an assumption must be made as to which part of the length of a columnar element is in contact with the next. Then, using the area occupied by each binding partner, it is determined how many binding partners are in contact with each other. The power of a single bond is known. This allows the maximum binding force per area to be determined. It is possible by modifications in the functionalization of the surface to bind less binding partner at the surface and thus to achieve a lower adhesive force between the columnar elements.

Selectable parameters thus influence the restoring force:
length of the pillars (influence on L)
base area of the pillars (influence on I)
shape of pillars (influence on I)
material of the pillars (influence on E)
With influence on the adhesion:
shape of the pillars (influence on contact area)
type of bond (bond strength per unit area)
number of bindings per area (maximum is defined, reduction possible)

Possible combinations of materials and shapes would be e.g.

1: Example of a Soft Polymer:
Material: Chloroprene rubber (CR, Neoprene): E=700 kPa
Shape of the columns: round
Length of the columns: 15 μm
Diameter of the columns: 5 μm
Displacement of the columns: 8 μm
Return force: 6.1E-7 N
Binding: Streptavidin—Biotin (about 150 pN)
Adhesive force: approx. 4.2E-7 N
Here it was assumed that the contact area between the pillars is 50% of the length and 2 nm in width.

2: Example of an Extremely Soft Polymer:
Material: Polyacrylamide hydrogel: E=10 kPa
Shape of the columns: round
Length of the columns: 15 μm
Diameter of the columns: 5 μm
Displacement of the columns: 8 μm
Return force: 8.7E-9 N
Binding: Concanavalin A-mannose carbohydrate (about 47 pN)
Adhesive force: approx. 8.4E-9 N (at approx. 6.25% of the maximum surface coverage with Con A)
Here it was assumed that the contact area between the pillars is 50% of the length and 2 nm in width.

3: Example of Very Hard Polymer:
Material: silicone elastomer: E=20000 kPa
Shape of the columns: square
Length of the columns: 15 μm
Side length of the columns: 5 μm
Displacement of the columns: 8 μm
Return force: 2.9E-5 N
Binding: concanavalin A-mannose carbohydrate (about 47 pN)
Adhesive force: approx. 2.3E-5 N (at approx. 10% of the maximum surface coverage with Con A)
Here it was assumed that the contact area between the columns is 50% of the length and the total width of the columns.

4: Example of Cadherin Catch Bonds:
Material: silicone elastomer: E=20000 kPa
Shape of the columns: square
Length of the columns: 15 μm
Side length of the columns: 5 μm
Displacement of the columns: 8
Return force: 2.9E-5 N
Binding: cadherin catch bonds (about 27-32 pN)
Adhesive force: approx. 2.3E-5 N-3.7E-5 (at approx. 80% of the maximum surface coverage with cadherin)
Here it was assumed that the contact area between the columns is 50% of the length and the total width of the columns.

5: Example of Very Large Columns:
Material: silicone elastomer: E=20000 kPa
Shape of the columns: Square
Length of the columns: 400 μm
Side length of the columns: 100 μm
Displacement of the columns: 160 μm
Restoring force: 5E-3 N
Binding: concanavalin A-mannose carbohydrate (about 47 pN)
Adhesive force: 4.9E-3N (at approx. 4% of the maximum surface coverage with Con A)
Here it was assumed that the contact area between the columns is 50% of the length and the total width of the columns.

Since in each case the maximum forces of the bonds are given, it is possible to work with a higher concentration of surface modification, or softer polymers and thus compensate for differences.

Preferred moduli of elasticity of the elastomers is between 10 kPa and 20000 kPa.

The strength of the bonds varies from 5 pN for hydrogen bonding to 150 pN for streptavidin-biotin binding.

Cadherin catch bonds vary between 27 and 32 pN.

The preferred diameter of the columns is between 4 and 100 μm. The preferred length is between 10 and 400 microns and the preferred center-to-center distance is 8.8 to 220 microns.

It is preferred that the spacing of the column sides from each other is about 10% of the column thickness.

The length to thickness ratio of the columns should preferably be at most 4:1.

Further information for further explanation:

A formula (curve function) for the bend line of the columns can be found.

$$w(x) = S_Q \cdot \{3 \cdot [x/L_0]^2 - 2 \cdot [x/L_0]^3\}$$

with $S_q$: displacement of the columns and $L_0$: length of the columns

With the help thereof it can be determined, at which displacement/bending, contact between the column occurs. It should be noted that the curve describes a neutral fiber in the center of the column. The curve of the outer edges is determined by means of corresponding curves parallel to the curve in the middle. If this is calculated, it turns out that for the example system with columns of 5 μm diameter, 15 μm length and a center-center distance of 5.5 µm at a bend of 8 µm there is a contact area of about 50% of the column length.

If 50% of the column length of square columns adhere to one another, the resulting system can be described as follows:

The non-adherent part of each column (one part above the adhered part and one part below) is a one-quarter length column.

So in this system, two columns with a quarter of the original length have been created. Both columns must be shifted by the length x/2 for a displacement of the system by the length x. Since the $1/L^3$ restoring force depends on the column length, the force needed to bend the system after the columns are stuck will be 64 times as high as before.

In the following, the production of a layer according to the invention will be described by way of example after determining the parameters according to the method.

For this example, a hexagonal array of round pillars with a diameter of 4.5 µm and center-to-center spacing of 10 µm is selected on a 3×3 mm area.
Material: Polydimethylsiloxane (PDMS) modulus E=1720 kPa (from Palchesko doi: 10.1371/journal.pone.0051499)
Shape of the columns: round
Length of the columns: 15 µm
Diameter of the columns: 4.5 µm
Column displacement: 6.5 µm
Return force: 3.26E-7
Binding: biotin streptavidin (about 150 pN)
Adhesive force: 3.20E-7 (at 75% of the maximum surface coverage with streptavidin)

Here it was assumed that the contact area between the pillars is 50% of the length and 2 nm in width.

First, the production of the mold takes place. A photoresist SU-8 10 from Microchem is spin-coated onto a 4" silicon wafer. The thickness of the paint determines the length of the later columns Different coatings from Microchem can represent different layer thicknesses. For the selected layer thickness of 15 µm, the SU-8 10 is very well suited.

In a lithographic process, holes are produced in this photoresist that correspond to the negative of the later columns. The structures on the photomask thus determine the arrangement and shape of the holes in the photoresist, which later correspond to the columns.

In order to prevent subsequent adhesion of the PDMS to the mold, an anti-adhesion layer is applied, in this case a monolayer of trichloro(1H,1H,2H,2H-perfluorooctyl) silanes.

Now the casting of the mold with PDMS is done. PDMS (Sylgard 184 from Dow), which is offered as a two-component kit consisting of base polymer and crosslinker, is mixed in the ratio (10:1 w/w polymer:crosslinker). This is recommended by the manufacturer. Other conditions lead to different values for the modulus of elasticity. The more crosslinker used, the harder the elastomer becomes. Less crosslinker softens the polymer. This means that the modulus of elasticity is lower.

The mixed polymer is placed on a Menzel cover slip and the mold is placed on top. Subsequently, the polymer is cured for one hour at 100° C.

The process is repeated to produce an identical sub-layer.

Figure 3:
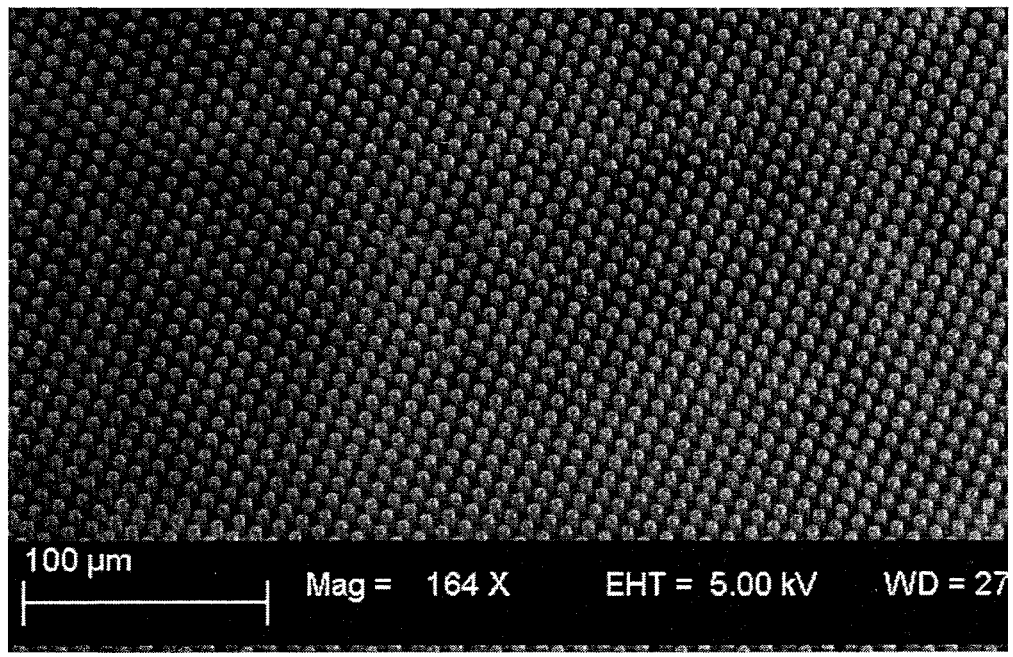

FIG. 3 shows an electron micrograph of the columns produced with a diameter of 4.5 microns and a center-to-center distance of 10 microns.

A partial structure is coated with biotin according to the following reaction scheme.

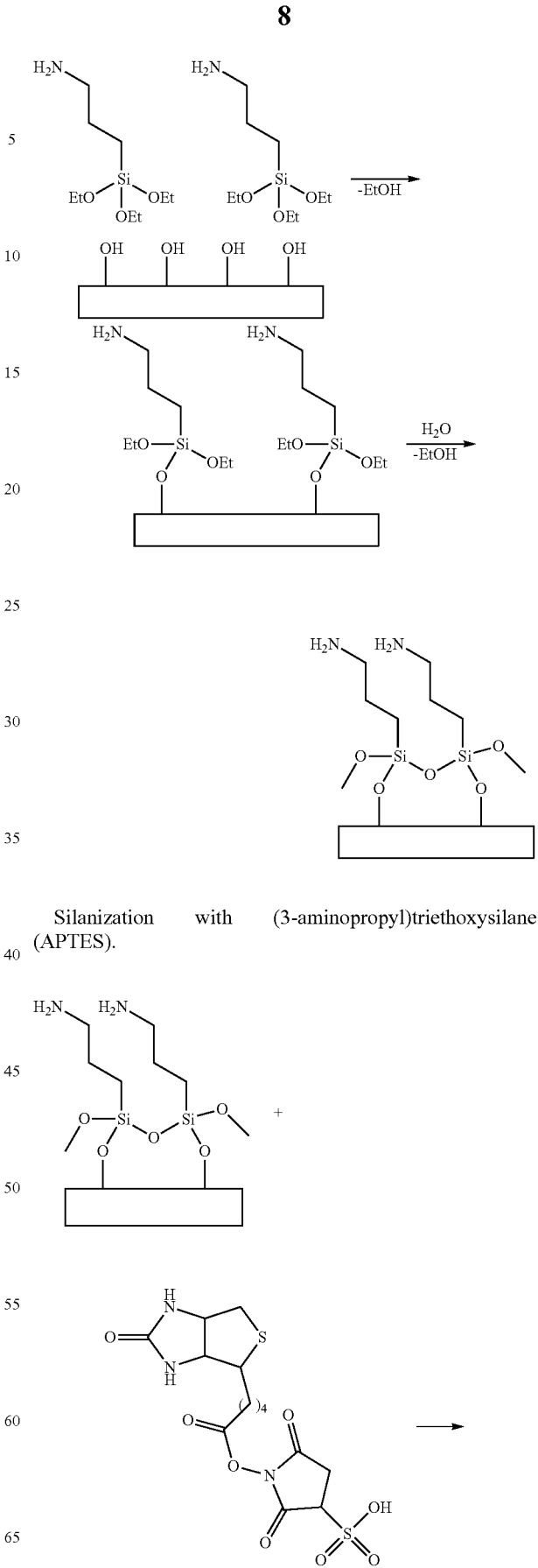

Silanization with (3-aminopropyl)triethoxysilane (APTES).

-continued

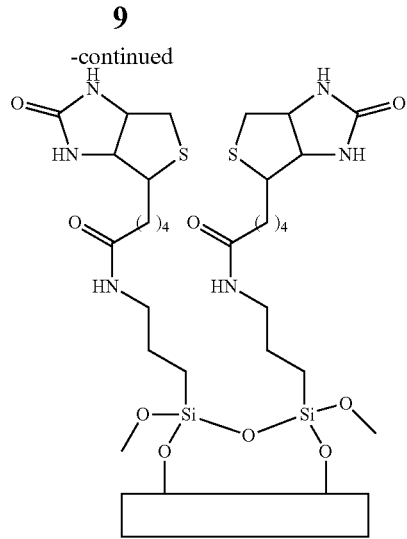

Connection of Biotin

The polymer is first activated in oxygen plasma and silanized with (3-aminopropyl)-triethoxysilane (APTES).

Biotin 3-sulfo-N-hydroxysuccinimide ester sodium salt is then covalently attached via the formation of an amide to the amino groups of the APTES.

The second substructure to produce the appropriate sublayer is, according to Kim et al. Biomicrofluidics 7, 041501 (2013) coated with streptavidin. Here, after a plasma treatment (3-mercaptopropyl) trimethoxysilane is selected for silanization. Biotin 3-sulfo-N-hydroxysuccinimide ester sodium salt is then covalently attached via the formation of an amide to the amino groups of the APTES. According to Mudraboyina et al. Sensors 2011, 11, 11295-11304; doi: 10.3390/s111211295, likewise in Kim et al. Biomicrofluidics 7, 041501 (2013), glutaraldehyde is used to establish a covalent bond between the amino groups in the protein (streptavidin) and on the surface. This does not affect the functionality of streptavidin.

Both structures are placed, after prior immersion of the column tips in not cured PDMS thinly distributed on a wafer, into each other and cured. The process is shown schematically in FIG. 4.

The goal of this step is to place biotin-coated columns (7) and streptavidin-coated columns (8) as close to each other as possible (9). This is due to the fact that it is not possible to coat only one column with biotin and the next one with streptavidin. For this reason, one surface modification per substructure is carried out in each case and then two partial layers are interlaced. If you look at the hexagonal structure with column spacings of 10 µm center-to-center, then the distance between the column walls is exactly 5.5 µm. If you now put the streptavidin structure exactly in the gaps between the biotin columns, then you have rows each with 0.5 micron intervals between each of a biotin column and a stretavidin column. These can then touch when exposed to a force and deflection. Biotin and streptavidin bind reversibly to each other.

As "glue" (6), uncrosslinked PDMS is used. This combines perfectly with the PDMS of the columns during curing.

Figure 2:
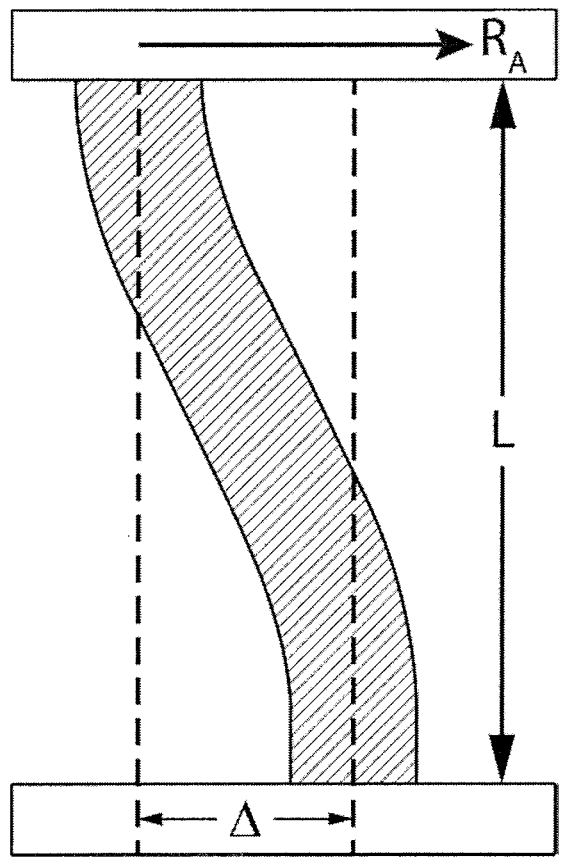

In the following, embodiments of the invention will be described in detail in the description of the figures with reference to the accompanying drawings, which are intended to illustrate the invention and are not to be considered as limiting:

There is shown in:

FIG. 1 principle of the layer according to the invention;

FIG. 2 graphical representation of important parameters for the method according to the invention;

FIG. 3 electron micrograph of a columnar structure of PDMS. The columnar elements have a diameter of 4.5 µm and a center-to-center distance of 10 µm.

Figure 4:
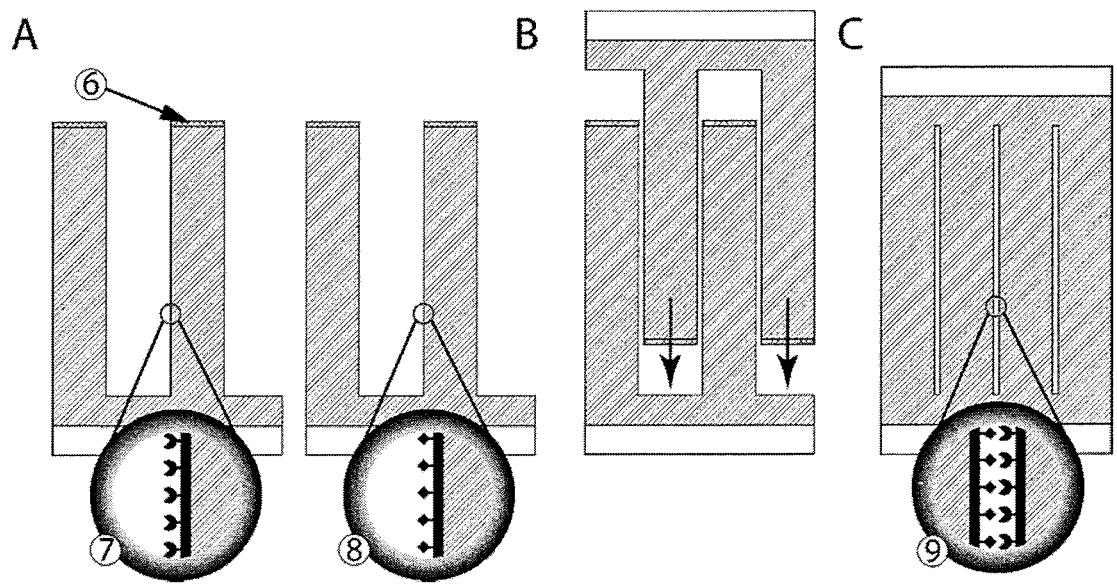

FIG. 4 merging of two structures with a column diameter of 4.5 µm and a center-to-center distance of 10 microns to a layer according to the invention with 0.5 µm distance between the columns

LIST OF REFERENCE NUMBERS

| | | | |
|---|---|---|---|
| 1 | columnar elements | 2 | surface modification |
| 3 | support material | 4 | cover plate |
| 5 | external force | 6 | adhesive |
| 7 | biotin coating | 8 | streptavidin coating |
| 9 | biotin and streptavidin coated columns close together | | |

The invention claimed is:

1. A variable strength layer comprising individual columnar elements of elastic material, their length exceeding their diameter, each columnar element having a base end and an opposite end and sides, which columnar elements are fixed with their base end at a defined distance from each other on a support and with their opposite end to a cover plate,
wherein the sides of the columnar elements are laterally movable towards or away from one another during movement of the cover plate relative to the support while their base ends and opposite ends, respectively, are prevented from moving towards or away from each other due to the fixation of their base ends to the support and opposite ends to the cover plate, wherein the sides of the elements can touch each other when moving towards each other,
wherein the outer surfaces of the columnar elements are provided with surface modification containing substances capable of forming reversible, non-covalent bonds upon interacting with substances applied to adjacent columnar element surfaces to form the reversible, non-covalent bonds, the substances selected from the group comprising protein A and antibodies, concanavalin A and α-D-glucose or streptavidin and biotin, or supramolecular structures with hydrogen bonds, π-π stacks, metal-ligand systems, or ionomers, wherein the substances are applied to columnar element surfaces such that they interact with substances applied to adjacent element surfaces upon contact to form the reversible, non-covalent bonds, and
wherein the variable strength layer is so constructed that the stiffness of the layer increases abruptly upon application of an external force causing contacting of surfaces of adjacent columnar elements and formation of reversible, non-covalent bonds between of the substances of the surface modification, and returns to its original flexible state upon release of this external force due to separation of contacting surfaces of columnar elements and separation of the reversible, non-covalent bonds between of the substances of the surface modification.

2. A variable strength layer comprising individual columnar elements of elastic material, their length exceeding their diameter, each columnar element having a base end and an opposite end and sides, which columnar elements are fixed with their base end at a defined distance from each other on a support and with their opposite end to a cover plate,
- wherein the sides of the columnar elements are laterally movable towards or away from one another during movement of the cover plate relative to the support while their base ends and opposite ends, respectively, are prevented from moving towards or away from each other due to the fixation of their base ends to the support and opposite ends to the cover plate, wherein the sides of the elements can touch each other when moving towards each other,
- wherein the outer surfaces of the elements are provided with a surface modification containing substances capable of forming reversible, non-covalent bonds upon interacting with substances applied to adjacent element surfaces to form the reversible, non-covalent bonds,
- such that upon application of an external force causing contacting of surfaces of adjacent columnar elements the layer stiffens abruptly due to formation of reversible, non-covalent bonds between of the substances of the surface modification, and upon cessation of the external force, the layer immediately returns to an original flexibility due to separation of contacting surfaces of columnar elements and separation of the reversible, non-covalent bonds between of the substances of the surface modification.

3. The layer according to claim 2, wherein thickness of the layer is less than 100 µm.

4. The layer according to claim 1, wherein thickness of the layer is less than 100 µm.

5. A shock-absorbing layer comprising individual columnar elements of elastic material, their length exceeding their diameter, each columnar element having a base end and an opposite end and sides, which columnar elements are fixed with their base end at a defined distance from each other on a support and with their opposite end to a cover plate,
- wherein the sides of the columnar elements are laterally movable towards or away from one another during movement of the cover plate relative to the support while their base ends and opposite ends, respectively, are prevented from moving towards or away from each other due to the fixation of their base ends to the support and opposite ends to the cover plate, wherein the sides of the elements can touch each other when moving towards each other,
- wherein the outer surfaces of the columnar elements are provided with surface modification containing substances capable of forming reversible, non-covalent bonds upon interacting with substances applied to adjacent columnar element surfaces to form the reversible, non-covalent bonds, the substances selected from the group comprising protein A and antibodies, concanavalin A and α-D-glucose or streptavidin and biotin, or supramolecular structures with hydrogen bonds, π-π stacks, metal-ligand systems, or ionomers, wherein the substances are applied to columnar element surfaces such that they interact with substances applied to adjacent element surfaces upon contact to form the reversible, non-covalent bonds, and
- wherein the shock-absorbing layer is so constructed that the stiffness of the layer increases abruptly upon application of an abrupt external force causing contacting of surfaces of adjacent columnar elements and formation of reversible, non-covalent bonds between of the substances of the surface modification, and abruptly returns to its original flexible state upon release of this external force due to separation of contacting surfaces of columnar elements and separation of the reversible, non-covalent bonds between of the substances of the surface modification.

* * * * *